United States Patent
Villace Lozano et al.

(10) Patent No.: US 11,905,324 B2
(45) Date of Patent: Feb. 20, 2024

(54) FLUORESCENT FUSION POLYPEPTIDE CAPABLE OF DETECTING PHOSPHORYLATION OF CELLULAR MEMBRANE RECEPTORS BY GRKS (G-PROTEIN RECEPTOR KINASES) AND/OR RECEPTOR TYROSINE KINASES (RTKS)

(71) Applicant: Innovative Technologies in Biological Systems SL, Derio-Bizkaia (ES)

(72) Inventors: Patricia Villace Lozano, Derio-Bizkaia (ES); Rosa Maria Mella Lopez, Derio-Bizkaia (ES); Danel Kortazar Zaballa, Derio-Bizkaia (ES); Jorge Gamiz Mata, Derio-Bizkaia (ES); Aida Clarisa Salado Pogonza, Derio-Bizkaia (ES)

(73) Assignee: INNOVATIVE TECHNOLOGIES IN BIOLOGICAL SYSTEMS SL, Derio Bizkaia (ES)

( * ) Notice: Subject to any disclaimer, the term of this patent is extended or adjusted under 35 U.S.C. 154(b) by 1119 days.

(21) Appl. No.: 16/483,657

(22) PCT Filed: Feb. 6, 2018

(86) PCT No.: PCT/EP2018/052944
§ 371 (c)(1),
(2) Date: Aug. 5, 2019

(87) PCT Pub. No.: WO2018/141987
PCT Pub. Date: Aug. 9, 2018

(65) Prior Publication Data
US 2019/0359686 A1 Nov. 28, 2019

(30) Foreign Application Priority Data
Feb. 6, 2017 (EP) .................................... 17382049

(51) Int. Cl.
| | |
|---|---|
| *C12N 9/88* | (2006.01) |
| *C07K 14/715* | (2006.01) |
| *C07K 14/47* | (2006.01) |
| *G01N 33/50* | (2006.01) |
| *G01N 33/542* | (2006.01) |

(52) U.S. Cl.
CPC ...... *C07K 14/7155* (2013.01); *C07K 14/4703* (2013.01); *G01N 33/5035* (2013.01); *G01N 33/542* (2013.01); *C07K 2319/03* (2013.01); *C07K 2319/60* (2013.01); *G01N 2333/726* (2013.01)

(58) Field of Classification Search
CPC ............ C07K 14/7155; C07K 14/4703; C07K 2319/03; C07K 2319/60; G01N 33/5035; G01N 33/542; G01N 2333/726

USPC .......................................................... 506/10
See application file for complete search history.

(56) References Cited

FOREIGN PATENT DOCUMENTS

| WO | WO 2014/006225 A1 * | 7/2013 | ............. C07K 14/47 |
|---|---|---|---|
| WO | 2014/006225 A1 | 1/2014 | |

OTHER PUBLICATIONS

Laporte et al: Proc. Natl. Acad. Sci. USA "The b2-adrenergic receptor/B-arrestin complex recruits the clathrin adaptor AP-2 during endocytosis," vol. 96, pp. 3712-3717 (Year: 1999).*
Oakley et al: ASSAY and Drug Development Technologies, "The cellular distribution of fluorescently labeled arrestins provides a robust, sensitive, and universal assay for screening G protein-coupled receptors,", vol. 1 No. 1-1, pp. 21-30 (Year: 2002).*
Laporte et al., "The B2-adrenergic receptor/βarrestin complex recruits the clathrin adaptor AP-2 during endocytosis," Proc. Natl. Acad. Sci. USA 96(7):3712-3717, 1999.
Oakley et al., "The cellular distribution of fluorescently labeled arrestins provides a robust, sensitive, and universal assay for screening G protein-coupled receptors," ASSAY and Drug Development Technologies 1(1-1):21-30, 2002.
Snapp, "Design and use of fluorescent fusion proteins in cell biology," NIH Public Access Author Manuscript, Curr Protoc Cell Biol. Chapter: Unit—21.4, 2005 (17 pages).

* cited by examiner

*Primary Examiner* — Tekchand Saidha
(74) *Attorney, Agent, or Firm* — SEED INTELLECTUAL PROPERTY LAW GROUP LLP

(57) ABSTRACT

The authors of the present invention designed a new fluorescent fusion polypeptide comprising a membrane localization peptide, a peptide capable of binding G-protein or tyrosine receptors following phosphorylation of these receptors by GRKs or RTKs, a vesicularization peptide and a fluorescent peptide. This biosensor is formed by two peptides targeted to two different cellular compartments, allowing the detection of the translocation of GRKs (G-protein receptor kinases) and/or beta-arrestin or Receptor tyrosine kinases (RTKs) from the cell cytoplasm to the cell cytoplasmic membrane in vivo by monitoring the distribution of the fluorescent polypeptide within the cellular cytoplasm. In this sense, the biosensor translocation within the cell shall be due to a change in its 3D conformation that hides or exposes the location signals in both ends of the polypeptide triggered by the binding of the peptide capable of binding G-protein or tyrosine receptors following phosphorylation of these receptors to the phosphorylated G-protein or tyrosine receptors.

8 Claims, 6 Drawing Sheets
Specification includes a Sequence Listing.

SEQUENCE LISTING

```
<160> NUMBER OF SEQ ID NOS: 4

<210> SEQ ID NO 1
<211> LENGTH: 1701
<212> TYPE: DNA
<213> ORGANISM: Artificial Sequence
<220> FEATURE:
<223> OTHER INFORMATION: phosphorylated receptor binding peptide from
      b-arrestin

<400> SEQUENCE: 1
atggacagct acctgctgat gtggggcctg ctgaccttca tcatggtgcc cggctgccag      60
gccgagctgt gcgacgacga cccccctgag atccccacg ccaccttcaa agccatggcc     120
tacaaagaag gcaccatgct gaactgcgag tgcaagcggg gcttccggcg gatcaagagc     180
ggcagcctgt acatgctgtg caccggcaac agcagccaca gcagctggga caaccagtgc     240
cagtgcacca gcagcgccac ccggaacacc accaaacagg tcacacccca gcccgaggaa     300
cagaaagagc gcaagaccac cgagatgcag agccccatgc agcccgtgga ccaggcctct     360
ctgcccggcc actgcagaga gcccccacct tgggagaacg aggccaccga gcggatctac     420
cacttcgtgg tcggacagat ggtgtactac cagtgcgtgc agggctaccg ggccctgcac     480
agaggacctg ccgagagcgt gtgcaagatg acccacggca agaccggtg gacccagccc     540 cagctgatct gcaccggcga gatggaaacc agccagttcc ccggcgagga aaagcccag      600 gccagccctg agggcagacc cgagagcgag acaagctgcc tggtgacaac caccgacttc     660
cagatccaga ccgagatggc cgccacaatg gaaacctcca tcttcaccac cgacctgcag     720
gtggccgtgg ccggctgcgt gttcctgctg atctctgtgc tgctcctgag cggcctgacc     780
tggcagcgga gacagagaaa gagcggccgg accatcggga tccaactagt tgtcgaccag     840
cagcagcagc agcagggaat tctgcagtcg acggtaccaa tggtgggtga ggatagcgag     900
```

```
ctgatcaccg agaacatgca catgaaactg tacatggagg gcaccgtgaa caaccaccac    960
ttcaagtgca catccgaggg cgaaggcaag ccctacgagg gcacccagac catgaagatc   1020
aaggtggtcg agggcggccc tctccccttc gccttcgaca tcctggctac cagcttcatg   1080
tacggcagca aagccttcat caaccacacc cagggcatcc ccgacttctt taagcagtcc   1140
ttccctgagg gcttcacatg ggagagaatc accacatacg aagacggggg cgtgctgacc   1200
gctacccagg acaccagcct ccagaacggc tgcctcatct acaacgtcaa gatcaacggg   1260
gtgaacttcc catccaacgg ccctgtgatg cagaagaaaa cactcggctg ggaggccagc   1320
accgagatgc tgtaccccgc tgacagcggc ctgagaggcc atggccagat ggccctgaag   1380
ctcgtgggcg ggggctacct gcactgctcc ctcaagacca catacagatc caagaaaccc   1440
gctaagaacc tcaagatgcc cggcttccac ttcgtggacc acagactgga aagaatcaag   1500
gaggccgaca agagaccta cgtcgagcag cacgagatgg ctgtggccaa gtactgcgac   1560
ctccctagca aactggggca cagcagatct cgagtaggcg cgcggcggcta tggccgtgaa   1620 gacctggatg tgctgggctt gtccttccgc aaagacctgg gcggcctcat tgaatttggc   1680
ggcggccggc ttcggctgaa g                                             1701
```

<210> SEQ ID NO 2
<211> LENGTH: 567
<212> TYPE: PRT
<213> ORGANISM: Artificial Sequence
<220> FEATURE:
<223> OTHER INFORMATION: phosphorylated receptor binding peptide from b-arrestin

<400> SEQUENCE: 2

```
Met Asp Ser Tyr Leu Leu Met Trp Gly Leu Leu Thr Phe Ile Met Val
1               5                   10                  15

Pro Gly Cys Gln Ala Glu Leu Cys Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Lys Ser Gly Ser Leu Tyr
    50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
    130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
        195                 200                 205
```

-continued

Ser Glu Thr Ser Cys Leu Val Thr Thr Asp Phe Gln Ile Gln Thr
    210                 215                 220

Glu Met Ala Ala Thr Met Glu Thr Ser Ile Phe Thr Thr Asp Leu Gln
225                 230                 235                 240

Val Ala Val Ala Gly Cys Val Phe Leu Leu Ile Ser Val Leu Leu Leu
            245                 250                 255

Ser Gly Leu Thr Trp Gln Arg Arg Gln Arg Lys Ser Gly Arg Thr Ile
        260                 265                 270

Gly Ile Gln Leu Val Val Asp Gln Gln Gln Gln Gln Gly Ile Leu
        275                 280                 285

Gln Ser Thr Val Pro Met Val Gly Glu Asp Ser Glu Leu Ile Thr Glu
290                 295                 300

Asn Met His Met Lys Leu Tyr Met Glu Gly Thr Val Asn Asn His His
305                 310                 315                 320

Phe Lys Cys Thr Ser Glu Gly Glu Gly Lys Pro Tyr Glu Gly Thr Gln
                325                 330                 335

Thr Met Lys Ile Lys Val Val Glu Gly Gly Pro Leu Pro Phe Ala Phe
            340                 345                 350

Asp Ile Leu Ala Thr Ser Phe Met Tyr Gly Ser Lys Ala Phe Ile Asn
        355                 360                 365

His Thr Gln Gly Ile Pro Asp Phe Phe Lys Gln Ser Phe Pro Glu Gly
    370                 375                 380

Phe Thr Trp Glu Arg Ile Thr Thr Tyr Glu Asp Gly Gly Val Leu Thr
385                 390                 395                 400

Ala Thr Gln Asp Thr Ser Leu Gln Asn Gly Cys Leu Ile Tyr Asn Val
                405                 410                 415

Lys Ile Asn Gly Val Asn Phe Pro Ser Asn Gly Pro Val Met Gln Lys
            420                 425                 430

Lys Thr Leu Gly Trp Glu Ala Ser Thr Glu Met Leu Tyr Pro Ala Asp
        435                 440                 445

Ser Gly Leu Arg Gly His Gly Gln Met Ala Leu Lys Leu Val Gly Gly
    450                 455                 460

Gly Tyr Leu His Cys Ser Leu Lys Thr Thr Tyr Arg Ser Lys Lys Pro
465                 470                 475                 480

Ala Lys Asn Leu Lys Met Pro Gly Phe His Phe Val Asp His Arg Leu
                485                 490                 495

Glu Arg Ile Lys Glu Ala Asp Lys Glu Thr Tyr Val Glu Gln His Glu
            500                 505                 510

Met Ala Val Ala Lys Tyr Cys Asp Leu Pro Ser Lys Leu Gly His Ser
        515                 520                 525

Arg Ser Arg Val Gly Gly Gly Tyr Gly Arg Glu Asp Leu Asp Val
    530                 535                 540

Leu Gly Leu Ser Phe Arg Lys Asp Leu Gly Gly Leu Ile Glu Phe Gly
545                 550                 555                 560

Gly Gly Arg Leu Arg Leu Lys
            565

<210> SEQ ID NO 3
<211> LENGTH: 272
<212> TYPE: PRT
<213> ORGANISM: Artificial Sequence
<220> FEATURE:
<223> OTHER INFORMATION: extracellular domain of interleukin-2 receptor

<400> SEQUENCE: 3

```
Met Asp Ser Tyr Leu Leu Met Trp Gly Leu Thr Phe Ile Met Val
1               5                   10                  15

Pro Gly Cys Gln Ala Glu Leu Cys Asp Asp Pro Pro Glu Ile Pro
                20                  25                  30

His Ala Thr Phe Lys Ala Met Ala Tyr Lys Glu Gly Thr Met Leu Asn
            35                  40                  45

Cys Glu Cys Lys Arg Gly Phe Arg Arg Ile Lys Ser Gly Ser Leu Tyr
        50                  55                  60

Met Leu Cys Thr Gly Asn Ser Ser His Ser Ser Trp Asp Asn Gln Cys
65                      70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
                100                 105                 110

Met Gln Pro Val Asp Gln Ala Ser Leu Pro Gly His Cys Arg Glu Pro
            115                 120                 125

Pro Pro Trp Glu Asn Glu Ala Thr Glu Arg Ile Tyr His Phe Val Val
            130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
                180                 185                 190

Phe Pro Gly Glu Glu Lys Pro Gln Ala Ser Pro Glu Gly Arg Pro Glu
            195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Asp Leu Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Gly Arg Thr Ile
            260                 265                 270

<210> SEQ ID NO 4
<211> LENGTH: 31
<212> TYPE: PRT
<213> ORGANISM: Artificial Sequence
<220> FEATURE:
<223> OTHER INFORMATION: Chlatrin and beta-adaptin peptide from arrestin

<400> SEQUENCE: 4

Tyr Gly Arg Glu Asp Leu Asp Val Leu Gly Leu Ser Phe Arg Lys Asp
1               5                   10                  15

Leu Gly Gly Leu Ile Glu Phe Gly Gly Gly Arg Leu Arg Leu Lys
            20                  25                  30
```

FLUORESCENT FUSION POLYPEPTIDE CAPABLE OF DETECTING PHOSPHORYLATION OF CELLULAR MEMBRANE RECEPTORS BY GRKS (G-PROTEIN RECEPTOR KINASES) AND/OR RECEPTOR TYROSINE KINASES (RTKS)

CROSS-REFERENCE TO RELATED APPLICATIONS

This application is a 371 of PCT/EP2018/052944, filed Feb. 6, 2018, which claims priority to European Patent Application No. EP17382049.9 filed Feb. 6, 2017, which is hereby incorporated by reference as if fully set forth herein.

FIELD OF THE INVENTION

The present invention pertains to the biotechnological field, particularly to a fluorescent fusion polypeptide, a biosensor comprising said polypeptide and uses thereof.

BACKGROUND OF THE INVENTION

Bioluminescence resonance energy transfer (BRET) is a powerful and increasingly popular technique for studying protein-protein interactions in live cells and real time. In particular, there has been considerable interest in the ability to monitor interactions between G protein-coupled receptors (GPCRs) and proteins that serve as key regulators of receptor function, such as beta-arrestin. The BRET methodology involves heterologous co-expression of genetically fused proteins that link one protein of interest (e.g., a GPCR) to a bioluminescent donor enzyme and a second protein of interest (e.g., beta-arrestin) to an acceptor fluorophore. If the fusion proteins are in close proximity, resonance energy will be transferred from the donor to the acceptor molecule and subsequent fluorescence from the acceptor can be detected at a characteristic wavelength. Such fluorescence is therefore indicative of the proteins of interest linked to the donor and the acceptor interacting directly or as part of a complex. In addition to monitoring protein-protein interactions to elucidate cellular function, BRET also has the potential to become an important technique for live cell high-throughput screening for drugs targeting GPCRs, utilizing ligand-induced interactions with beta-arrestins.

However, these types of biosensors are highly dependent on the distance between (e.g. <10 nm for CFP/YFP) and the relative orientation of donor and acceptor fluorophore. In addition, BRET or FRET-based biosensors in the context of high content screening methods requires of a detection equipment of at least four filters, two for the excitation and two for the emission. In addition, due to the low intensity of the detection signal, the detection signal range and the screening sensibility are low. Lastly, the use of more than one fluorescence emission signal requires the use of more algorithms in order to correctly analyse the final signal.

Thus, there is still a need to develop improved methods or products for real time measurement of protein-protein interactions in live cells such as interactions between G protein-coupled receptors (GPCRs) and proteins that serve as key regulators of receptor function, such as beta-arrestin.

BRIEF DESCRIPTION OF THE INVENTION

The present invention confronts the problem of providing tools of precise localization, high dynamic range and as little disturbance of cell physiology as possible that are capable of monitoring a variation in the translocation of GRKs (G-protein receptor kinases) and/or beta-arrestin or Receptor tyrosine kinases (RTKs) from the cell cytoplasm to the cell cytoplasmic membrane in vivo by using High-content screening (HCS) in cell-based systems, wherein these tools do not have the disadvantages of FRET-based biosensors.

In order to solve the above problem, the authors of the present invention designed a new fluorescent fusion polypeptide comprising a membrane localization peptide, a peptide capable of binding G-protein or tyrosine receptors following phosphorylation of these receptors by GRKs or RTKs, a vesicularization peptide and a fluorescent peptide. This biosensor is formed by two peptides targeted to two different cellular compartments, allowing the detection of the translocation of GRKs (G-protein receptor kinases) and/or beta-arrestin or Receptor tyrosine kinases (RTKs) from the cell cytoplasm to the cell cytoplasmic membrane in vivo by monitoring the distribution of the fluorescent polypeptide within the cellular cytoplasm. In this sense, the biosensor translocation within the cell shall be due to a change in its 3D conformation that hides or exposes the location signals in both ends of the polypeptide triggered by the binding of the peptide capable of binding G-protein or tyrosine receptors following phosphorylation of these receptors to the phosphorylated G-protein or tyrosine receptors.

BRIEF DESCRIPTION OF THE FIGURES

The accompanying drawings, which are incorporated in and constitute a part of this specification, illustrate several embodiments and together with the description illustrate the disclosed compositions and methods.

DETAILED DESCRIPTION OF THE INVENTION

Figure 1:
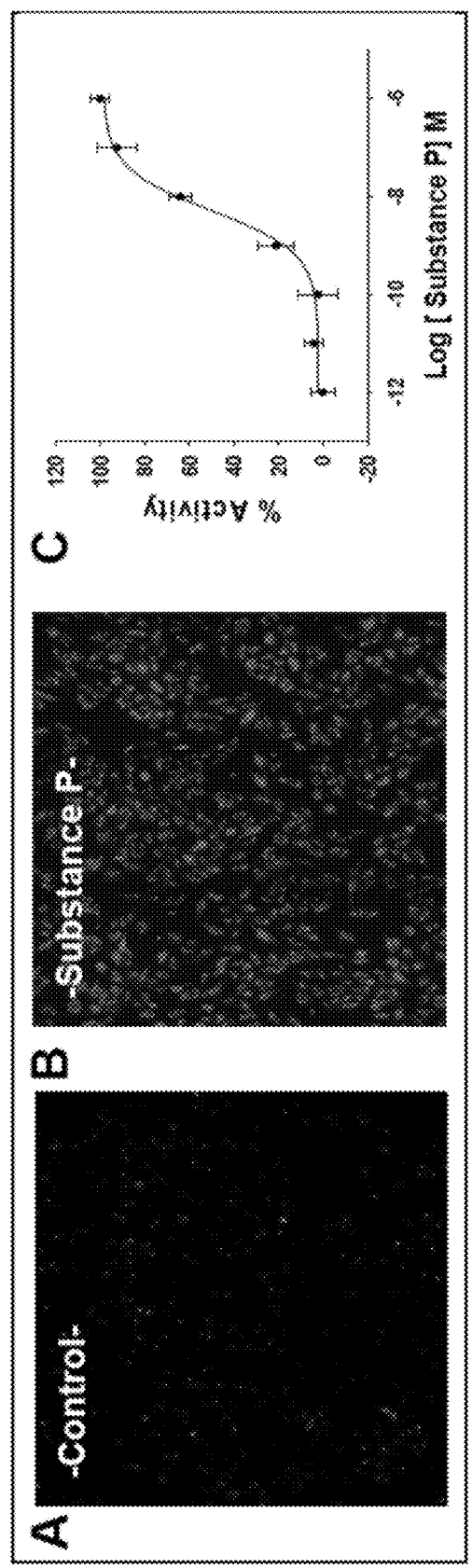
FIG. 1. Overview of the increase in the fluorescence of "NK1-Red ß-ARRNomad biosensor" cell line (A) Negative control. (B) Substance P 1 μM stimulated cells. (C) Dose response curve.
Figure 2:
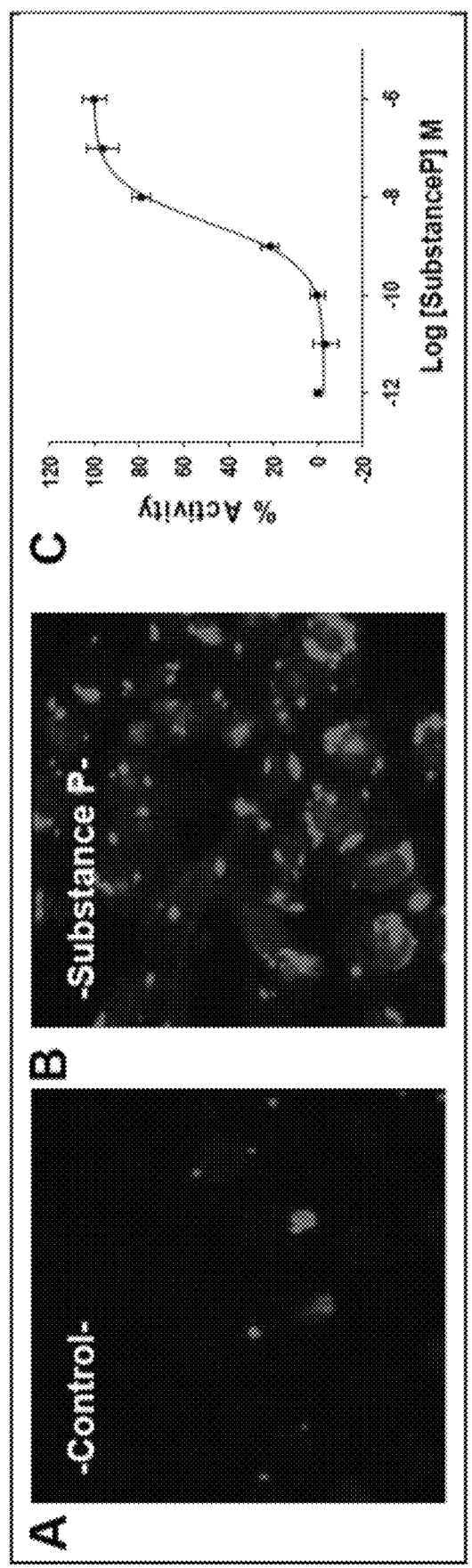
FIG. 2. Image analysis of "NK1-Red ß-ARRNomad biosensor" cell line (A) Negative control. (B) Substance P 1 μM stimulated cells. (C) Dose response curve.
Figure 3:
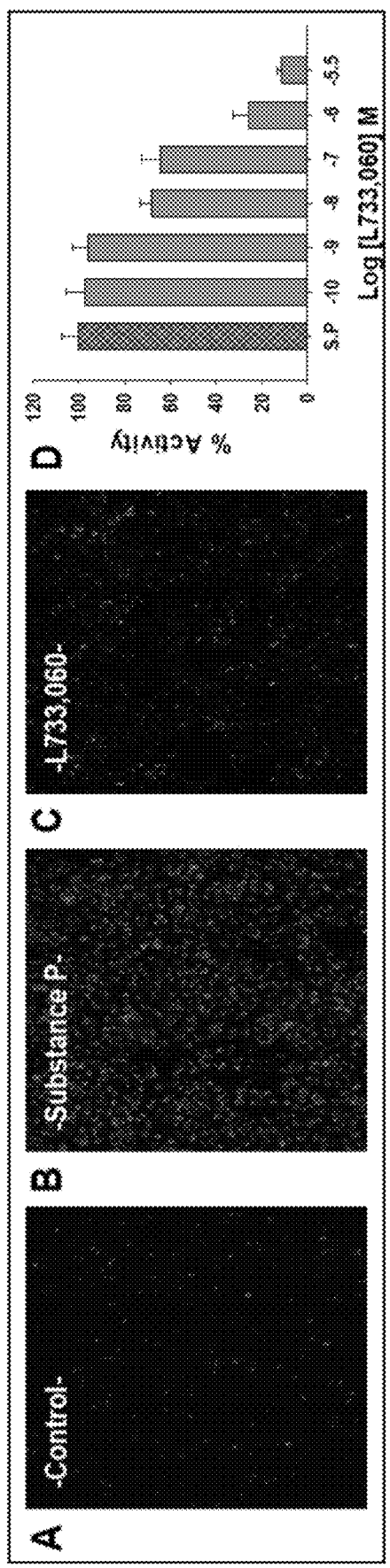
FIG. 3. Inhibition assay of "NK1-Red ß-ARRNomad biosensor" cell line (A) Negative control. (B) Substance P 1 μM stimulated cells. (C) L733,060 inhibited cells. (C) Inhibition plot.
Figure 4:
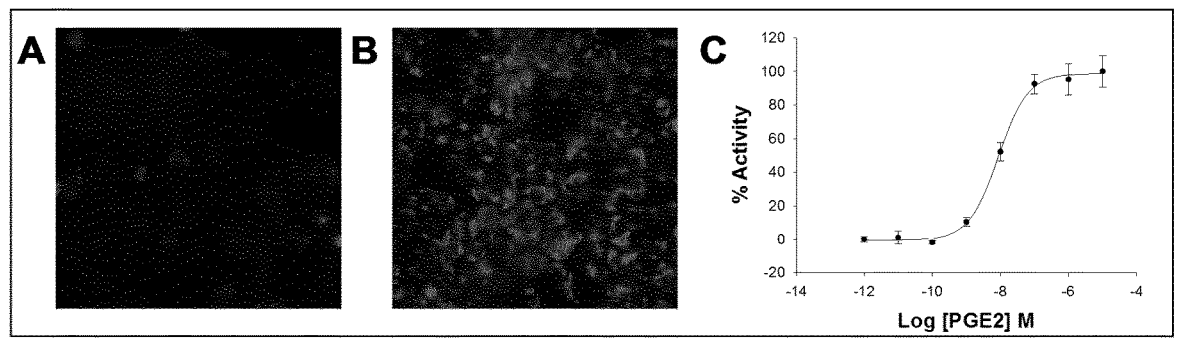
FIG. 4. Overview of the increase in the fluorescence of "$EP_4$ receptor Red $_{Arrestin}$Nomad biosensor" in the HEK293 cell line (A) Negative control. (B) PGE2 10 μM stimulated cells. (C) Dose response curve. $Ec_{50}$ PGE2=$8.64 \times 10^{-9}$M; Z'=0.67
Figure 5:
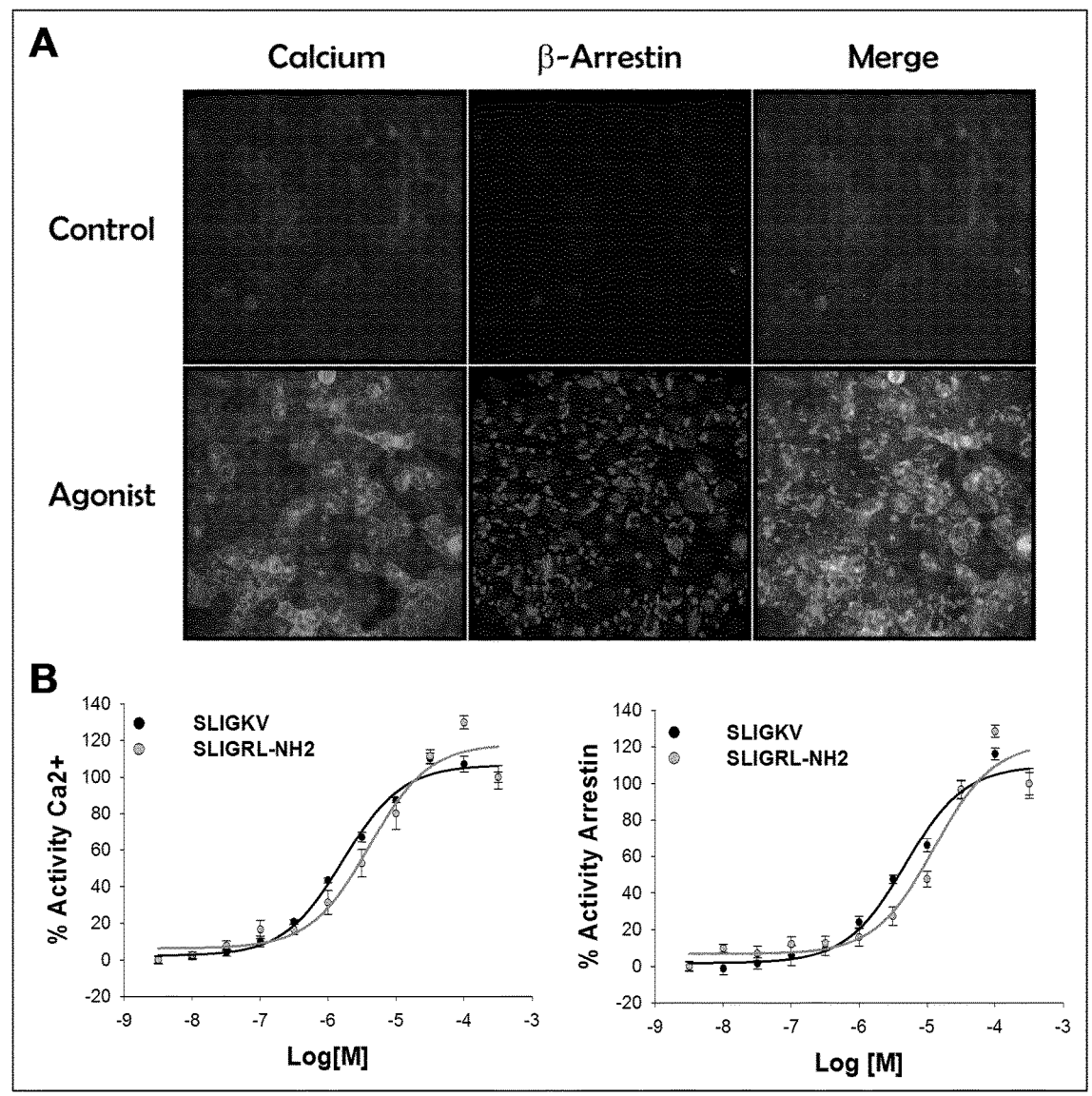
FIG. 5. Image analysis of $Ca^{2+}$-Arrestin Multiplex "PAR2 $_{Arres-Ca2+}$ Nomad biosensor" in the U2OS cell line (A) Overview of the increase in the fluorescence of green $_{Ca2+}$Nomad biosensor (left panel), red $_{Arrestin}$Nomad biosensor (middle panel) and merge (right panel) (B) Dose response curves of each biosensors with two different agonists of PAR2 receptor.
Figure 6:
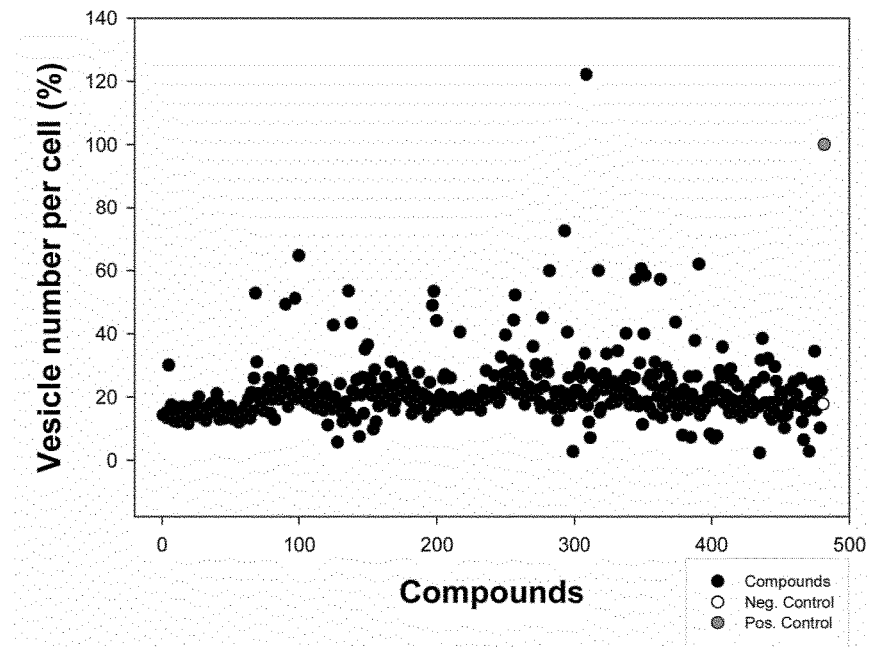
FIG. 6. Screening of a 490 compounds library using the NK1R $_{Arrestin}$Nomad U2OS cell line. Representative data of vesicle number per cell normalized to the control. The negative control (DMSO) is represented in white and the positive control (Substance P 10 μM) in green.
Figure 7:
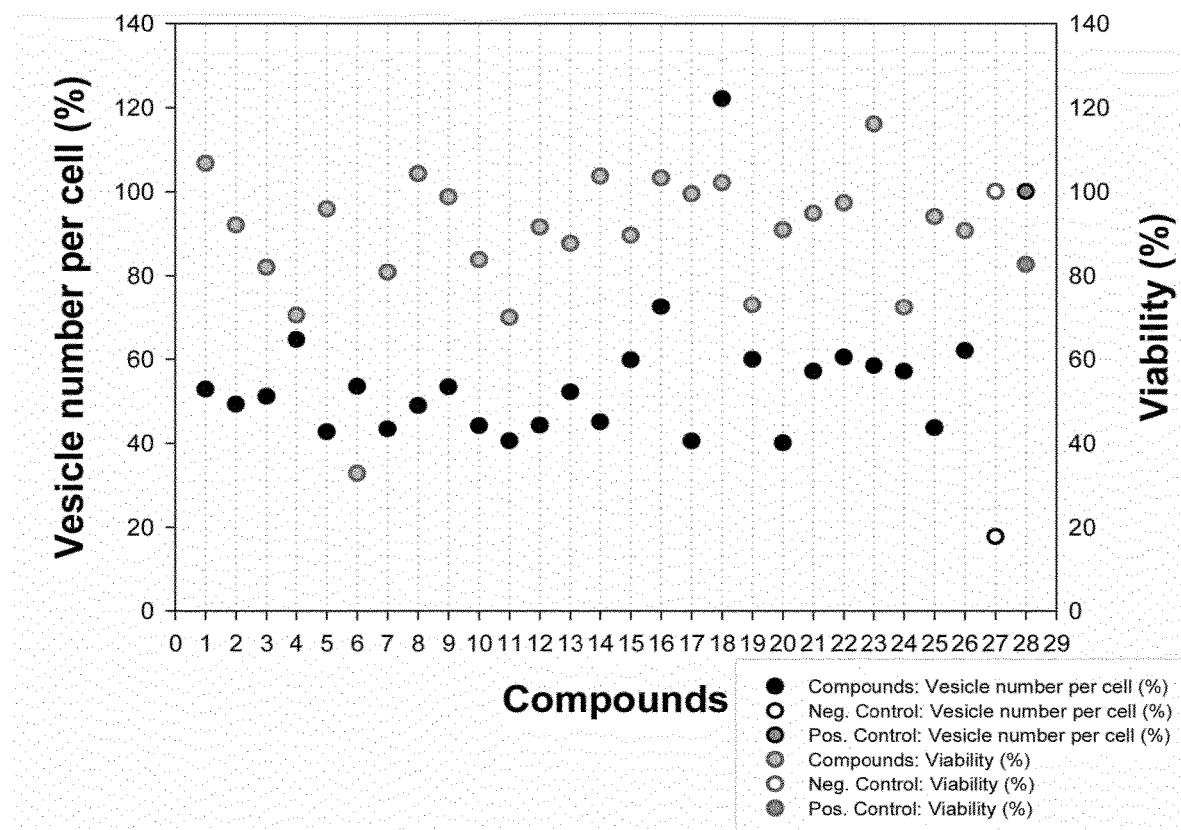
FIG. 7. Positive compounds. The compounds that show an increment in the arrestin pathway activation are represented in black and the cell viability percentage is represented in white. The positive control (Substance P) is represented in green spots and the negative control (DMSO) is represented in white.
Figure 8:
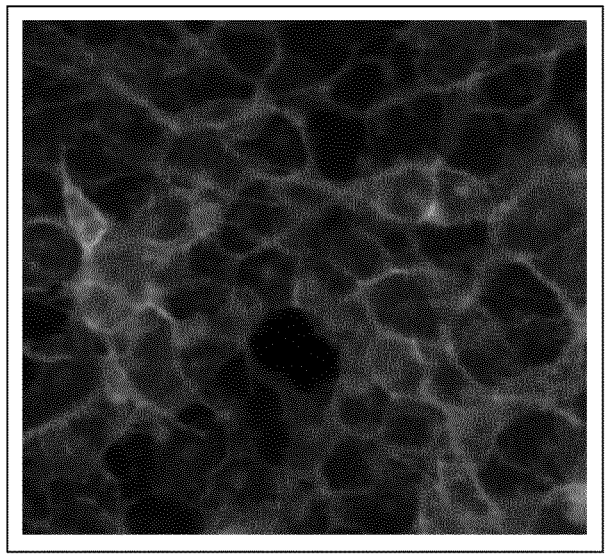
FIG. 8. NomadKin. Membrane localization of NomadKin biosensor in U2OS cell line.
Figure 9:
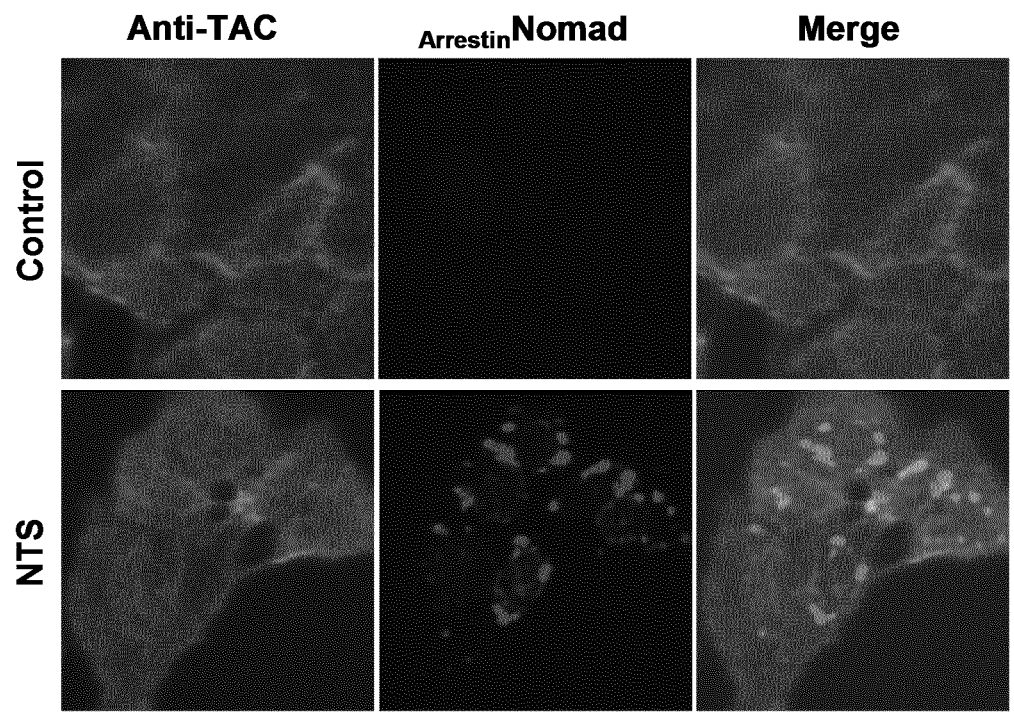
FIG. 9. Anti-tac Immunofluorescence assay of "NTSR1 $_{Arrestin}$Nomad biosensor. $_{Arrestin}$Nomad biosensor is located in the plasma membrane in basal conditions (upper panel) after the addition of the agonist (NTS, 1 μM) it can be observed a relocalization of the biosensor from the plasma membrane to vesicle trafficking pathways (lower panel).

Unless expressly specified otherwise, the term "comprising" is used in the context of the present document to indicate that further members may optionally be present in addition to the members of the list introduced by "comprising". It is, however, contemplated as a specific embodiment of the present invention that the term "comprising" encompasses the possibility of no further members being present, i.e. for the purpose of this embodiment "comprising" is to be understood as having the meaning of "consisting of".

Definitions

In the context of the present invention, the term "fusion polypeptide" refers to a hybrid polypeptide comprising a combination of at least four peptides from different proteins that are combined into the same polypeptide structure.

In the context of the present invention, the term "membrane localization peptide" is intended to mean a peptide whose natural intracellular localization is in the plasma membrane.

As used herein, the term "peptide capable of binding G-protein or tyrosine receptors following phosphorylation of these receptors by GRKs or RTKs" is intended to mean a peptide or protein domain that has the ability to interact with the G-protein or tyrosine receptors only when these are phosphorylated. A clear example of such peptide is the phosphorylated receptor binding peptide from b-arrestin of SEQ ID 2.

It is noted that the nucleotide sequence coding for the phosphorylated receptor binding peptide of SEQ ID NO: 2 is as follows:

```
(SEQ ID NO: 1)
atggacagct acctgctgat gtggggcctg ctgaccttca tcatggtgcc cggctgccag    60
gccgagctgt gcgacgacga ccccctgag atccccacg ccaccttcaa agccatggcc    120
tacaaagaag gcaccatgct gaactgcgag tgcaagcggg gcttccggcg gatcaagagc    180
ggcagcctgt acatgctgtg caccggcaac agcagccaca gcagctggga caaccagtgc    240
cagtgcacca gcagcgccac ccggaacacc accaaacagg tcacacccca gcccgaggaa    300
cagaaagagc gcaagaccac cgagatgcag agcccatgc agcccgtgga ccaggcctct    360
ctgcccggcc actgcagaga gcccccacct tgggagaacg aggccaccga gcggatctac    420
cacttcgtgg tcggacagat ggtgtactac cagtgcgtgc agggctaccg ggccctgcac    480
agaggacctg ccgagagcgt gtgcaagatg acccacggca agaccggtg gacccagccc    540 cagctgatct gcaccggcga gatggaaacc agccagttcc ccggcgagga aaagcccag    600 gccagccctg agggcagacc cgagagcgag acaagctgcc tggtgacaac caccgacttc    660
cagatccaga ccgagatggc cgccacaatg gaaacctcca tcttcaccac cgacctgcag    720
gtggccgtgg ccggctgcgt gttcctgctg atctctgtgc tgctcctgag cggcctgacc    780
tggcagcgga gacagagaaa gagcggccgg accatcggga tccaactagt tgtcgaccag    840
cagcagcagc agcagggaat tctgcagtcg acggtaccaa tggtgggtga ggatagcgag    900
ctgatcaccg agaacatgca catgaaactg tacatggagg gcaccgtgaa caaccaccac    960
ttcaagtgca catccgaggg cgaaggcaag ccctacgagg gcacccagac catgaagatc   1020
aaggtggtcg agggcggccc tctcccttc gccttcgaca tcctggctac cagcttcatg   1080
tacggcagca aagccttcat caaccacacc cagggcatcc ccgacttctt taagcagtcc   1140
ttccctgagg gcttcacatg ggagagaatc accacatacg aagacggggg cgtgctgacc   1200
gctacccagg acaccagcct ccagaacggc tgcctcatct acaacgtcaa gatcaacggg   1260
gtgaacttcc catccaacgg ccctgtgatg cagaagaaaa cactcggctg ggaggccagc   1320
accgagatgc tgtaccccgc tgacagcggc ctgagaggcc atggccagat ggccctgaag   1380
ctcgtgggcg ggggctacct gcactgctcc ctcaagacca catacagatc caagaaaccc   1440
gctaagaacc tcaagatgcc cggcttccac ttcgtggacc acagactgga aagaatcaag   1500
gaggccgaca aagagaccta cgtcgagcag cacgagatgg ctgtggccaa gtactgcgac   1560
ctccctagca aactggggca cagcagatct cgagtaggcg gcggcggcta tggccgtgaa   1620
```

```
gacctggatg tgctgggctt gtccttccgc aaagacctgg gcggcctcat tgaatttggc    1680
ggcggccggc ttcggctgaa g                                              1701
```

(SEQ ID NO: 2):

```
Met Asp Ser Tyr Leu Leu Met Trp Gly Leu Leu Thr Phe Ile Met Val
Pro Gly Cys Gln Ala Glu Leu Cys Asp Asp Pro Pro Glu Ile Pro
His Ala Thr Phe Lys Ala Met Ala Tyr Lys Glu Gly Thr Met Leu Asn
Cys Glu Cys Lys Arg Gly Phe Arg Arg Ile Lys Ser Gly Ser Leu Tyr
Met Leu Cys Thr Gly Asn Ser Ser His Ser Ser Trp Asp Asn Gln Cys
Gln Cys Thr Ser Ser Ala Thr Arg Asn Thr Thr Lys Gln Val Thr Pro
Gln Pro Glu Glu Gln Lys Glu Arg Lys Thr Thr Glu Met Gln Ser Pro
Met Gln Pro Val Asp Gln Ala Ser Leu Pro Gly His Cys Arg Glu Pro
Pro Pro Trp Glu Asn Glu Ala Thr Glu Arg Ile Tyr His Phe Val Val
Gly Gln Met Val Tyr Tyr Gln Cys Val Gln Gly Tyr Arg Ala Leu His
Arg Gly Pro Ala Glu Ser Val Cys Lys Met Thr His Gly Lys Thr Arg
Trp Thr Gln Pro Gln Leu Ile Cys Thr Gly Glu Met Glu Thr Ser Gln
Phe Pro Gly Glu Glu Lys Pro Gln Ala Ser Pro Glu Gly Arg Pro Glu
Ser Glu Thr Ser Cys Leu Val Thr Thr Thr Asp Phe Gln Ile Gln Thr
Glu Met Ala Ala Thr Met Glu Thr Ser Ile Phe Thr Thr Asp Leu Gln
Val Ala Val Ala Gly Cys Val Phe Leu Leu Ile Ser Val Leu Leu Leu
Ser Gly Leu Thr Trp Gln Arg Arg Gln Arg Lys Ser Gly Arg Thr Ile
Gly Ile Gln Leu Val Val Asp Gln Gln Gln Gln Gln Gly Ile Leu
Gln Ser Thr Val Pro Met Val Gly Glu Asp Ser Glu Leu Ile Thr Glu
Asn Met His Met Lys Leu Tyr Met Glu Gly Thr Val Asn Asn His His
Phe Lys Cys Thr Ser Glu Gly Glu Gly Lys Pro Tyr Glu Gly Thr Gln
Thr Met Lys Ile Lys Val Val Glu Gly Gly Pro Leu Pro Phe Ala Phe
Asp Ile Leu Ala Thr Ser Phe Met Tyr Gly Ser Lys Ala Phe Ile Asn
His Thr Gln Gly Ile Pro Asp Phe Phe Lys Gln Ser Phe Pro Glu Gly
Phe Thr Trp Glu Arg Ile Thr Thr Tyr Glu Asp Gly Gly Val Leu Thr
Ala Thr Gln Asp Thr Ser Leu Gln Asn Gly Cys Leu Ile Tyr Asn Val
Lys Ile Asn Gly Val Asn Phe Pro Ser Asn Gly Pro Val Met Gln Lys
Lys Thr Leu Gly Trp Glu Ala Ser Thr Glu Met Leu Tyr Pro Ala Asp
Ser Gly Leu Arg Gly His Gly Gln Met Ala Leu Lys Leu Val Gly Gly
Gly Tyr Leu His Cys Ser Leu Lys Thr Thr Tyr Arg Ser Lys Lys Pro
Ala Lys Asn Leu Lys Met Pro Gly Phe His Phe Val Asp His Arg Leu
Glu Arg Ile Lys Glu Ala Asp Lys Glu Thr Tyr Val Glu Gln His Glu
Met Ala Val Ala Lys Tyr Cys Asp Leu Pro Ser Lys Leu Gly His Ser
Arg Ser Arg Val Gly Gly Gly Gly Tyr Gly Arg Glu Asp Leu Asp Val
Leu Gly Leu Ser Phe Arg Lys Asp Leu Gly Gly Leu Ile Glu Phe Gly
Gly Gly Arg Leu Arg Leu Lys
```

As used herein, the term "vesicularization peptide" is intended to mean a short peptide chain that directs the transport of the polypeptide to the retention vesicles. Preferably such vesicularization peptide is the Clathrin and beta-adaptin peptide from arrestin. More preferably, the peptide sequence for the Clathrin and beta-adaptin peptide from arrestin is as follows (from hereinafter SEQ ID NO: 4):

Tyr Gly Arg Glu Asp Leu Asp Val Leu Gly Leu Ser

Phe Arg Lys Asp Leu Gly Gly Leu Ile Glu Phe Gly

Gly Gly Arg Leu Arg Leu Lys

As used herein, the term "fluorescent peptide" is intended to mean a fluorescent peptide that has fluorescent capacities. Fluorescent peptide domains are characterized by having a specific excitation spectrum and emission spectrum.

In the context of the present invention, the linker has at least one amino acid residue, preferably at least two consecutive amino acid residues.

As used herein, the term "biosensor" is intended to mean a molecular tool or entity that is sensitive to, and can respond to, a physical or chemical stimulus and transmit information about cellular status.

As used herein, the term "drug" is intended to mean a molecule that potentially acts as an agonist or antagonist or modulator of a signalling pathway.

As used herein "stable cell line" is intended to mean a cell line that has been transfected or infected with a foreign piece of DNA that has incorporated itself into the genome of the cell.

DESCRIPTION

The present invention confronts the problem of providing tools of precise localization, high dynamic range and as little disturbance of cell physiology as possible that are capable of monitoring a variation in the translocation of GRKs (G-protein receptor kinases) and/or beta-arrestin or Receptor tyrosine kinases (RTKs) from the cell cytoplasm to the cell cytoplasmic membrane in vivo by using High-content screening (HCS) in cell-based systems, wherein these tools do not have the disadvantages of FRET-based biosensors.

In order to solve the above problem, the authors of the present invention designed a new fluorescent fusion polypeptide comprising a membrane localization peptide, a peptide capable of binding G-protein or tyrosine receptors following phosphorylation of these receptors by GRKs or RTKs, a vesicularization peptide and a fluorescent peptide. This biosensor is formed by two peptides targeted to two different cellular compartments, allowing the detection of the translocation of GRKs (G-protein receptor kinases) and/or beta-arrestin or Receptor tyrosine kinases (RTKs) from the cell cytoplasm to the cell cytoplasmic membrane in vivo by monitoring the distribution of the fluorescent polypeptide within the cellular cytoplasm. In this sense, the biosensor translocation within the cell shall be due to a change in its 3D conformation that hides or exposes the location signals in both ends of the polypeptide triggered by the binding of the peptide capable of binding G-protein or tyrosine receptors following phosphorylation of these receptors to the phosphorylated G-protein or tyrosine receptors.

In the basal state, the biosensor is located in one of the compartments; this means that the location peptide directed to the other cellular compartment is hidden by the 3D conformation. When there is a translocation of GRKs (G-protein receptor kinases) and/or beta-arrestin or Receptor tyrosine kinases (RTKs) from the cell cytoplasm to the cell cytoplasmic membrane due to a cellular stimulation, the peptide capable of binding G-protein or tyrosine receptors following phosphorylation of these receptors binds to the phosphorylated G-protein or tyrosine receptors causing a conformational change in the biosensor. At this point the spatial distribution of the different structural elements in the biosensor is modified and the vesicularization peptide directed to the other cellular compartment is exposed by the new 3D conformation so that the whole biosensor is transported to its new location at the new cellular compartment. All this process can be traced in living cells due to the presence of the fluorescent protein in the biosensor.

It is further noted, that the authors of the present invention realized that the order of the peptides within the above mentioned fluorescent fusion polypeptide could not be placed arbitrarily within the polypeptide. This is the case since after numerous experiments the authors concluded that only one combination of elements provided the technical effect of transporting the biosensor to the other cellular compartment, such combination was:

a. the membrane localization peptide is located at the N-terminus of the fluorescent fusion polypeptide and is physically bound, optionally through a linker, to the fluorescent peptide, which in turn is physically bound, optionally through a linker, to the peptide capable of binding G-protein or tyrosine receptors following phosphorylation of these receptors by GRKs or RTKs; and b. the peptide capable of binding G-protein or tyrosine receptors following phosphorylation of these receptors by GRKs or RTKs is physically bound, optionally through a linker, to the vesicularization peptide, which in turn is located at the C-terminus of the fluorescent fusion polypeptide;

The authors tested whether such biosensor having the above structure could be employ for detecting and quantifying the translocation of beta-arrestin caused by substance P. As illustrated in the examples disclosed herein, the authors of the present invention constructed a fluorescent fusion polypeptide, capable of detecting and quantifying beta-arrestin successfully, comprising the phosphorylated receptor binding peptide from b-arrestin of SEQ ID 2. Surprisingly, the authors identified that by using as a vesicularization peptide the Clathrin and beta-adaptin peptide from arrestin, the detection signal was significantly better.

The results shown in the examples and drawings presented herein by using the above fusion polypeptide indicate that an increased in the translocation of beta-arrestin induced a conformational change in the biosensor which promoted a redistribution of the fluorescent biosensor. The activity was calculated as an increment of the granularity of the cells transfected with the biosensors of the invention. The fluorescence redistribution of the biosensor was detected by fluorescence using image analysis algorithms. Consequently, the variations in the location of the beta arrestin can be monitored through this "hiding and exposition" process of location signals and the final localization of the biosensor.

Thus, a first aspect of the present invention refers to a fluorescent fusion polypeptide capable of changing its localization within the cell from the cell cytoplasmic membrane to the retention vesicles, upon an increase in the translocation of GRKs (G-protein receptor kinases) and/or beta-arrestin or Receptor tyrosine kinases (RTKs) from the cell cytoplasm to the cell cytoplasmic membrane, comprising a membrane localization peptide, a peptide capable of binding G-protein or tyrosine receptors following phosphorylation of these receptors by GRKs or RTKs, a vesicularization peptide and a fluorescent peptide wherein:
a. the membrane localization peptide is located at the N-terminus of the fluorescent fusion polypeptide and is physically bound, optionally through a linker, to the fluorescent peptide, which in turn is physically bound, optionally through a linker, to the peptide capable of binding G-protein or tyrosine receptors following phosphorylation of these receptors by GRKs or RTKs; and
b. the peptide capable of binding G-protein or tyrosine receptors following phosphorylation of these receptors by GRKs or RTKs is physically bound, optionally through a linker, to the vesicularization peptide, which in turn is located at the C-terminus of the fluorescent fusion polypeptide;

and wherein the term "membrane localization peptide" is intended to mean a peptide whose natural intracellular localization is in the plasma membrane.

Preferably, such fluorescent fusion polypeptide is capable of changing its localization within the cell from the cell cytoplasmic membrane to the retention vesicles, upon an increase in the translocation of GRKs (G-protein receptor kinases) and beta-arrestin from the cell cytoplasm to the cell cytoplasmic membrane.

More preferably the fluorescent fusion polypeptide of the first aspect of the invention is characterized by:
a. the membrane localization peptide being the extracellular domain of interleukin-2 receptor of SEQ ID 3 or a variant which is at least 90% homologous to this sequence over the entire region based on amino acid identity; and
b. the vesicularization peptide being the Clathrin and beta-adaptin peptide from arrestin.

Amino acidic SEQ ID No: 3 is as follows:

```
Met Asp Ser Tyr Leu Leu Met Trp Gly Leu Leu Thr
Phe Ile Met Val Pro Gly Cys Gln Ala Glu Leu Cys
Asp Asp Asp Pro Pro Glu Ile Pro His Ala Thr Phe
Lys Ala Met Ala Tyr Lys Glu Gly Thr Met Leu Asn
Cys Glu Cys Lys Arg Gly Phe Arg Arg Ile Lys Ser
Gly Ser Leu Tyr Met Leu Cys Thr Gly Asn Ser Ser
His Ser Ser Trp Asp Asn Gln Cys Gln Cys Thr Ser
Ser Ala Thr Arg Asn Thr Thr Lys Gln Val Thr Pro
Gln Pro Glu Glu Gln Lys Glu Arg Lys Thr Thr Glu
Met Gln Ser Pro Met Gln Pro Val Asp Gln Ala Ser
Leu Pro Gly His Cys Arg Glu Pro Pro Pro Trp Glu
Asn Glu Ala Thr Glu Arg Ile Tyr His Phe Val Val
Gly Gln Met Val Tyr Tyr Gln Cys Val Gln Gly Tyr
Arg Ala Leu His Arg Gly Pro Ala Glu Ser Val Cys
Lys Met Thr His Gly Lys Thr Arg Trp Thr Gln Pro
Gln Leu Ile Cys Thr Gly Glu Met Glu Thr Ser Gln
Phe Pro Gly Glu Glu Lys Pro Gln Ala Ser Pro Glu
Gly Arg Pro Glu Ser Glu Thr Ser Cys Leu Val Thr
```
-continued
```
Thr Thr Asp Phe Gln Ile Gln Thr Glu Met Ala Ala
Thr Met Glu Thr Ser Ile Phe Thr Thr Asp Leu Gln
Val Ala Val Ala Gly Cys Val Phe Leu Leu Ile Ser
Val Leu Leu Leu Ser Gly Leu Thr Trp Gln Arg Arg
Gln Arg Lys Ser Gly Arg Thr Ile
```

More preferably the fluorescent fusion polypeptide of the first aspect of the invention is characterized by:
a. the membrane localization peptide being the extracellular domain of interleukin-2 receptor of SEQ ID 3; and
b. the vesicularization peptide being the Clathrin and beta-adaptin peptide from arrestin, preferably of SEQ ID No: 4.

More preferably the fluorescent fusion polypeptide of the first aspect of the invention is characterized by:
a. the membrane localization peptide being the extracellular domain of interleukin-2 receptor of SEQ ID 3;
b. the vesicularization peptide being the Chlatrin or beta-adaptin peptide from arrestin, preferably of SEQ ID No: 4; and
c. the peptide capable of binding G-protein receptors following phosphorylation of these receptors by GRKs, being the phosphorylated receptor binding peptide from b-arrestin of SEQ ID 2.

In yet another preferred embodiment of the first aspect of the invention, such polypeptide is capable of changing its localization within the cell from the cell cytoplasmic membrane to the retention vesicles, upon an increase in the translocation of Receptor tyrosine kinases (RTKs) from the cell cytoplasm to the cell cytoplasmic membrane.

More preferably the fluorescent fusion polypeptide of the above mentioned preferred embodiment of the invention (the biosensor capable of detecting an increased an increase in the translocation of Receptor tyrosine kinases (RTKs) from the cell cytoplasm to the cell cytoplasmic membrane) is characterized by:
a. the membrane localization peptide is the extracellular domain of interleukin-2 receptor of SEQ ID 3 or a variant which is at least 90% homologous to this sequence over the entire region based on amino acid identity; and
b. the vesicularization peptide is the Clathrin and beta-adaptin peptide from arrestin.

More preferably the fluorescent fusion polypeptide of the above mentioned preferred embodiment of the invention (the biosensor capable of detecting an increased an increase in the translocation of Receptor tyrosine kinases (RTKs) from the cell cytoplasm to the cell cytoplasmic membrane) is characterized by:
a. the membrane localization peptide is the extracellular domain of interleukin-2 receptor of SEQ ID 3; and
b. the vesicularization peptide is the Chlatrin and beta-adaptin peptide from arrestin, preferably of SEQ ID No: 4.

More preferably the fluorescent fusion polypeptide of the above mentioned preferred embodiment of the invention (the biosensor capable of detecting an increased an increase in the translocation of Receptor tyrosine kinases (RTKs) from the cell cytoplasm to the cell cytoplasmic membrane) is characterized by:
a. the membrane localization peptide being the extracellular domain of interleukin-2 receptor of SEQ ID 3;

b. the vesicularization peptide being the Clathrin and beta-adaptin peptide from arrestin, preferably of SEQ ID No: 4; and
c. the peptide capable of binding tyrosine-protein receptors following phosphorylation of these receptors by RTKs, being a peptide capable of recognizing the phosphorylated Receptor tyrosine protein.

It is noted that such peptide capable of recognizing the phosphorylated Receptor tyrosine protein, may comprised a SH2 domain and/or a domain designed in silico, any of these capable of recognizing phosphorylated tyrosin-kinase receptors. Such domains are well known to the skilled person.

In another preferred embodiment of the first aspect of the invention, the fluorescent fusion polypeptide may be selected from any of the following list of compounds consisting of GFP, YFP, turboGFP, turboRFP, turboRFP602 and turboFP650.

A second aspect of the invention refers to a nucleic acid molecule comprising a polynucleotide sequence coding for a polypeptide as defined in any of the previous aspects of the invention.

A third aspect of the invention refers to a biosensor comprising the fusion polypeptide as defined in the first aspect of the invention.

A fourth aspect of the invention refers to a cell comprising the fluorescent fusion polypeptide as defined in the first aspect of the invention, wherein preferably said cell is cell line U2OS (see examples).

In a further aspect, the present invention relates to several uses for the fluorescent fusion polypeptide as defined in the first aspect of the invention. A first use of the biosensor according to the present invention is for detecting and quantifying compounds capable of the translocation of GRKs (G-protein receptor kinases) and/or beta-arrestin or Receptor tyrosine kinases (RTKs) from the cell cytoplasm to the cell cytoplasmic membrane including, but not limited thereto, substance P. As already stated, binding the peptide capable of binding G-protein or tyrosine receptors following phosphorylation of these receptors binds to the phosphorylated G-protein or tyrosine receptors results in a substantial change in the spatial conformation that leads to a change in the intracellular fluorescence localization. This fluorescence translocation can be harnessed for compound quantification by fluorescence. In addition, all this process can be traced in living cells due to the presence of the fluorescent protein in the biosensor.

The employment of the fluorescent fusion polypeptide as defined in the first aspect of the invention further involves its use as a tool for drug screening.

In addition, the fluorescent fusion polypeptide as defined in the first aspect of the invention is useful in the practice of essentially any application for which readout of second messenger transduction is obtained. Such applications are well known in the art. However, more exemplary applications of the present invention include but are not limited to:
a. Identifying test compounds that act as agonists, antagonists, inverse agonists or natural ligands of cell surface receptor selected from growth factors, cytokines, G-protein coupled receptors, integrins and calcium ion channels by studying the second messenger movement using fluorescence microscopy devices. In a preferred embodiment, said cell surface receptor is a G-protein coupled receptor (GPCR).
b. Expression cloning of peptide agonist, antagonist and inverse agonist of receptors.
c. Expression cloning of modulators that change the second messenger intracellular presence.
d. Establishing dose-response curves of membrane molecules modulators.
e. Determining alterations in membrane molecules and modulators involved in a disease or disorder which signalling cascade depends on these second messengers and thereby the biosensor can be used as a diagnostic tool.

In a preferred embodiment of the invention, the fluorescent fusion polypeptide as defined in first aspect of the invention can be used to generate stable cell lines which allow studying G-protein coupled receptors (GPCR), and the activity of others proteins in living cells. The rapid translocation of the biosensor of the invention allows the quantification of GPCR and ion channel stimulation.

The fluorescent fusion polypeptide and the corresponding biosensor of the present invention can be made by techniques well known by those skilled in the art but as a way of example, they can be constructed as follows. The coding sequences corresponding to the membrane localization peptide, the fluorescent peptide, the peptide capable of binding G-protein or tyrosine receptors following phosphorylation of these receptors by GRKs or RTKs, and the vesicularization peptide can be easily amplified by PCR and cloned into a shuttle plasmid. These coding sequences can be then easily cloned into the final fusion plasmid in the specific order presented herein using the restriction enzyme sites that flanked each sequence.

The following examples merely serve to illustrate the present invention.

EXAMPLES

Example 1. Materials and Methods

Cell Culture of U2OS Cells

Human bone osteosarcoma cell line (DSMZ), derived from ATCC (Catalog No. HTB-96), was grown in Dulbecco's Modified Eagle's Medium Nutrient Mixture F-12 HAM (Sigma-Aldrich) supplemented with 10% Fetal Bovine Serum (Sigma-Aldrich), MEM non-essential amino acids (Sigma-Aldrich), gentamicin (Sigma-Aldrich), GENETICIN 500 µg/ml (Sigma-Aldrich) and Puromycin 10 µg/ml (Sigma) at 37° C. in a humidified atmosphere supplemented with 5% CO2.

Generation of Recombinant Stable Cell Line

Red ß-ARRNomad biosensor plasmid was created by subsequent cloning of the Tac cDNA, turboFP602 protein cDNA, (Evrogen), phosphorylated receptor binding peptide from b-arrestin, and the vesicularization peptide (Clathrin and beta-adaptin peptide from arrestin) into the GENETICIN resistant CMV-ptNL vector designed in our lab. Tachykinin receptor 1 (NK1) receptor's cDNA (cDNA.org) was subcloned in a Puromycin resistant vector, CMV-pPuro, designed in our lab using NheI and XhoI restriction enzymes.

All the clonings were confirmed by DNA sequencing. Plasmid containing Red ß ARRNomad biosensor was transfected into U2OS cells using LIPOFECTAMINE LTX (Invitrogen) and positive transfected cells were selected using 500 µg/ml GENETICIN (Sigma-Aldrich) the positive clone named C1 was transfected with the puromycin resistant plasmid containing Tachykinin receptor 1 (NK1-pPuro) and the positive clones were selected using 10 µg/ml puromicyn (Sigma-Aldrich) and 500 µg/ml GENETICIN (Sigma-Aldrich) Resistant clones were obtained by limit dilution. Double stable cell line, termed "NK1-Red ß-ARRNomad biosensor cell line" was then tested using Substance P (Sigma-Aldrich) for functional Red ß-ARRNomad biosensor response.

Development of the Assays

Cells were seeded at 18,000 cells/plate in 96-well black, clear-bottom imaging plates (BD Biosciences) for ß-arrestin assays. "NK1-Red ß-ARRNomad biosensor" cell line was treated with 8 log dilution (n=6) of Substance P (Sigma-Aldrich) ranging from 0 to 1 µM in OPTI-MEM media (Gibco) for 24 hours at 37° C., 5% CO2, 95% relative humidity before data acquisition.

Fluorescence Intensity Assay

For fluorescence intensity determinations, changes in the distribution of Red ß-ARRNomad biosensor were measured using "SYNERGY 2" microplate reader (Biotek). OPTI-MEM media with the agonists was removed and replaced by PBS 1× without calcium and magnesium (Sigma-Aldrich) before the data acquisition. TurboFP602 data were acquired with ex/em 590/620 filters.

Image Assay

The image analysis routine of the redistribution of Red ß-ARRNomad biosensor was developed with a BD PATHWAY 855 High-Content automated image platform (BD Biosciences) using image analysis algorithms with the Attovision bioimaging software (BD). Rhodamine excitation/emission filters used for image acquiring were 548/20 and 570LP. Calculated Nomad biosensor number of vesicles were normalized as percentage of activity compared to the negative control (vehicle H2O).

Inhibition Assay

Cells were seeded at 18,000 cells/plate in 96-well plates for inhibition assay. "NK1-Red ß-ARRNomad biosensor" cell line was co-treated with Substance P 100 nM (Sigma-Aldrich) and log dilution of L733,060 hydrochloride (Tocris) ranging from 100 µM to 3 µM in OPTI-MEM media (Gibco) for 24 hours at 37° C., 5% CO2, 95% relative humidity before data acquisition.

Z'Factor and Signal-to-Background Determination

The signal to background (S/B) parameter was calculated as µc+−µc−, and Z'factor was calculated using the following formula: $Z'=1-[(3\sigma c++3\sigma c-)/(\mu c+-\mu c-)]$.

Example 1. Results

"NK1-Red ß-ARRNomad biosensor" cell line stably expressing red ß-ARRNomad biosensor and Neurokinin receptor 1 has been designed to assay compounds or analyze its capability to modulate NK1 receptor. Before the stimulation mediated by the agonist of interest, the fluorescent biosensor is localized in the cellular membrane, the union of Substance P to Neurokinin 1 receptor leads to a change in the structural folding of Red ß-ARRNomad Biosensor that promotes its cellular relocation in the vesicular trafficking of the cells.

Fluorescence Intensity Assay

The increase in the fluorescence was detected and analyzed using "SYNERGY 2" microplate reader from Biotek. The Ec50 for the Substance P was approx. $5.20\times10^{-9}$ M after a treatment of 24 h with the agonist. The assay was validated with an average of Z'=0.70+/−0.02 (n=6).

Image Assay

Activation and Red ß-ARRNomad biosensor change of localization processes were detected and analyzed using "BD PATHWAY 855" High-Content Bioimager from BD Biosciences. The Ec50 for the Substance P was approx. $2.99\times10^{-9}$ M after a treatment of 24 h with the agonist. The assay was validated with an average of Z'=0.79+/−0.02 (n=6).

Inhibition Assay "NK1-Red ß-ARRNomad biosensor" cell line was co-treated with Substance P 100 nM and increasing concentrations of L733,060 (NKR1 inhibitor) during 24 h. After the treatment, nuclei were stained with DAPI and inhibition of NK1 receptor was detected analyzing Red ß-ARRNomad biosensor change of localization using "BD PATHWAY 855" High-Content Bioimager from BD Biosciences. The Ic50 for L733,060 was Approx. $1.84\times10^{-7}$ M after a treatment of 24 h with the agonist. The assay was validated with an average of Z'=0.66+/−0.02.

Example 2: $EP_4$ Receptor Red $_{Arrestin}$Nomad Biosensor" in the HEK293 Cell Line Example 2. Results "$EP_4$ receptor Red $_{Arrestin}$Nomad biosensor" HEK293 cell line transiently expressing red $_{Arrestin}$Nomad biosensor and prostaglandin E receptor 4 has been designed to assay compounds or analyze its capability to modulate $EP_4$ receptor. Before the stimulation mediated by the agonist of interest, the fluorescent biosensor is localized in the cellular membrane, the union of PGE2 to $EP_4$ receptor leads to a change in the structural folding of Red $_{Arrestin}$Nomad biosensor that promotes its cellular relocation in the vesicular trafficking of the cells. The Ec50 for the PGE2 was $8.64\times10^{-9}$ M after a treatment of 24 h with the agonist. The assay was validated with an average of Z'=0.67+/−0.04 (n=6).

Example 2. Materials and Methods

Cell Culture of HEK293 Cells

HEK293 cells derived from ATCC (Catalog No. CRL-1573), were grown in Dulbecco's Modified Eagle's Medium—high glucose (Sigma-Aldrich) supplemented with 10% Fetal Bovine Serum (Sigma-Aldrich), MEM non-essential amino acids (Sigma-Aldrich) and gentamicin (Sigma-Aldrich) at 37° C. in a humidified atmosphere supplemented with 5% CO2.

Generation of Transiently Transfected Cell Line

Red $_{Arrestin}$Nomad biosensor plasmid was created by subsequent cloning of the Tac cDNA, turboFP602 protein cDNA, (Evrogen), phosphorylated receptor binding peptide from b-arrestin, and the vesicularization peptide (Clathrin and beta-adaptin peptide from arrestin) into the GENETICIN resistant CMV-ptNL vector designed in our lab. $EP_4$ receptor ($EP_4$) receptor's cDNA (cDNA.org) was subcloned in a Puromycin resistant vector, CMV-pPuro, designed in our lab using NheI and XhoI restriction enzymes.

Transient transfection was performed using phosphate calcium method and the transiently transfected cell line, termed "$EP_4$-Red $_{Arrestin}$Nomad biosensor cell line" was then tested using PGE2 (Sigma-Aldrich) for functional Red $_{Arrestin}$Nomad biosensor response.

Development of the Assays

Cells were seeded at 20,000 cells/plate in 96-well black, clear-bottom imaging plates (BD Biosciences) for ß-arrestin assays. "$EP_4$-Red $_{Arrestin}$Nomad biosensor" cell line was treated with 8 log dilution (n=6) of PGE2 (Sigma-Aldrich) ranging from 0 to 10 µM in OPTI-MEM media (Gibco) for 24 hours at 37° C., 5% CO2, 95% relative humidity before data acquisition. Fluorescent images were acquired in the BD PATHWAY 855 High-Content automated image platform with a ×20 dry objective.

Fluorescence Intensity Assay

For fluorescence intensity determinations, changes in the distribution of Red ß-ARRNomad biosensor were measured using "SYNERGY 2" microplate reader (Biotek). OPTI-MEM media with the agonists was removed and replaced by PBS 1× without calcium and magnesium (Sigma-Aldrich) before the data acquisition. TurboFP602 data were acquired with ex/em 590/620 filters.

Z'Factor and Signal-to-Background Determination

The signal to background (S/B) parameter was calculated as µc+−µc−, and Z'factor was calculated using the following formula: $Z'=1-[(3\sigma_{c+}+3\sigma_{c-})/(\mu_{c+}-\mu_{c-})]$ Example 3: $Ca^{2+}$-Arrestin Multiplex "PAR2 $_{Arres-Ca2+}$Nomad Biosensor" in the U2OS Cell Line Example 3. Results $Ca^{2+}$-Arrestin Multiplex "PAR2 $_{Arres-Ca2+}$Nomad biosensor" in the U2OS cell line stably expressing green $_{Ca2+}$Nomad biosensor, red $_{Arrestin}$Nomad biosensor and F2R like trypsin receptor 1 has been designed to assay compounds or analyze its capability to modulate PAR2. Before the stimulation mediated by the agonists of interest, the fluorescent biosensor is localized in the cellular membrane, the union of SLIGKV or $SLIGRL-NH_2$ to PAR2 leads to a change in the structural folding of both Nomad biosensors that promotes their cellular relocation in the vesicular trafficking of the cells.

The increase in the fluorescence was detected and analyzed using the "SYNERGY 2" microplate reader from Biotek. The $Ec_{50}$ for the agonists was measured after a treatment of 24 h. The assay was validated with Z'>0.6 for each agonist.

| | |
|---|---|
| $EC_{50}$ SLIGKV β-Arrestin assay: 4.83 × $10^{-6}$M | $EC_{50}$ SLIGKV calcium assay: 1.67 × $10^{-6}$M |
| $EC_{50}$ SLIGRL-NH2 β-Arrestin assay: 1.27 × $10^{-5}$M | $EC_{50}$ SLIGRL-NH2 calcium assay: 4.06 × $10^{-6}$M |
| Z' SLIGKV$_{β-Arrestin}$: 0.85 +/− 0.01 | Z' SLIGKV$_{Calcium}$: 0.68 +/− 0.01 |
| Z' SLIGKRL-NH2$_{β-Arrestin}$: 0.75 +/− 0.01 | Z' SLIGRL-NH2$_{Calcium}$: 0.74 +/− 0.01 |

Example 3. Materials and Methods

Cell Culture of U2OS Cells

Human bone osteosarcoma cell line (DSMZ), derived from ATCC (Catalog No. HTB-96), was grown in Dulbecco's Modified Eagle's Medium Nutrient Mixture F-12 HAM (Sigma-Aldrich) supplemented with 10% Fetal Bovine Serum (Sigma-Aldrich), MEM non-essential amino acids (Sigma-Aldrich), gentamicin (Sigma-Aldrich) at 37° C. in a humidified atmosphere supplemented with 5% CO2.

Generation of Recombinant Stable Cell Line

The plasmid encoding the green $_{Ca2+}$Nomad biosensor was transfected into U2OS cells using LIPOFECTAMINE LTX (Thermo Fisher Scientific, Waltham, MA). Resistant clones were obtained by limit dilution, and positively transfected cells were selected using 10 µg/ml puromycin (Thermo Fisher Scientific, Waltham, MA). Once this stable cell line was ready, a positive clone was transfected with the plasmid encoding the red $_{Arrestin}$Nomad biosensor, and the positive clones were selected by limit dilution using 10 µg/ml puromycin (Thermo Fisher Scientific, Waltham, MA) and 500 µg/ml GENETICIN (Sigma-Aldrich, St. Louis, MO). The cell line co-expressing both biosensors, named $_{Arres-Ca2+}$Nomad cell line, was subsequently transfected with the PAR2-CMV-pHygro construction, and resistant clones were obtained by limit dilution and selected using 500 µg/ml GENETICIN (Sigma-Aldrich, St. Louis, MO), 10 µg/ml puromycin (Thermo Fisher Scientific, Waltham, MA) and 100 µg/ml hygromycin B (Thermo Fisher Scientific, Waltham, MA). These cells constitutively expressed green $_{Ca2+}$Nomad biosensor, red $_{Arrestin}$Nomad biosensor and the F2R like trypsin receptor 1, and this triple stable cell line was denominated the "PAR2 $_{Arres-Ca2+}$Nomad cell line".

Development of the Assays

Cells were seeded at 20,000 cells/plate in 96-well black, clear-bottom imaging plates (BD Biosciences) for $Ca^{2+}$ and Arrestin assays. "PAR2 $_{Arres-Ca2+}$Nomad" cell line was treated with 10 log dilution (n=6) of SLIGKV (Sigma-Aldrich) or $SLIGRL-NH_2$ (Sigma-Aldrich) ranging from 0 to 300 µM in OPTI-MEM media (Gibco) for 24 hours at 37° C., 5% CO2, 95% relative humidity before data acquisition. Fluorescent images were acquired in the BD PATHWAY 855 High-Content automated image platform with a ×20 dry objective.

Fluorescence Intensity Assay

For fluorescence intensity determinations, changes in the distribution of Red ß-ARRNomad biosensor were measured using "SYNERGY 2" microplate reader (Biotek). OPTI-MEM media with the agonists was removed and replaced by PBS 1× without calcium and magnesium (Sigma-Aldrich) before the data acquisition. TurboFP650 data were acquired with ex/em 590/650 filters and turboGFP lectures were captured with ex/em 485/585 filters.

Z'Factor and Signal-to-Background Determination

The signal to background (S/B) parameter was calculated as µc+−µc−, and Z'factor was calculated using the following formula: $Z'=1-[(3\sigma_{c+}+3\sigma_{c-})/(\mu_{c+}+\mu_{c-})]$ Example 4: High-Content Screening of the PRESTWICK CHEMICAL LIBRARY in NK1R $_{Arrestin}$Nomad U2OS Cell Line Example 4. Results A chemical library comprising 490 compounds was sourced from the PRESTWICK CHEMICAL LIBRARY®, and based on the compounds' chemical and pharmacological diversity and their bioavailability and safety for humans, these compounds were used for the screening assay. The reference compound was Substance P. All compounds from the library were dissolved in dimethyl sulfoxide (DMSO) at 5 mM and the reference compound in water at 1 mM. The NK1R$_{Arrestin}$Nomad U2OS cells were treated with Substance P (positive control) at 10 µM, whereas the compounds of the library were tested at 10 µM for 24 hours in OPTI-MEM media before image acquisition.

Example 4. Materials and Methods

Image acquisition and analysis: After 24 h of treatment, the cells were fixed with phosphate-buffered saline supplemented with 3.7% formaldehyde for 10 min at room temperature (RT) and permeabilized with 0.3% TRITON-X100 in PBS for 3 min at RT. The cell nuclei were then stained with DAPI for 5 min at RT. Fluorescent images were acquired in the BD PATHWAY 855 High-Content automated image platform with a ×20 dry objective. The changes in the fluorescence patterns of the $_{Arrestin}$Nomad biosensor were processed and quantified using image analysis algorithms with the Attovision bioimaging software in 3×3 subfields of each well (500-1,000 cells analyzed per well). The excitation and emission filters used were the following: for DAPI, 380/10 and 540/20 and for Rhodamine, 548/20 and 570LP. Arrestin activity was measured by counting the red fluorescent granules and normalizing the result to the cell number. The data were normalized as percentages of activity compared to the positive control (Substance P) after subtracting the value of the vehicle control. Cellular viability was determined by counting the nuclei (DAPI). For each condition, 5 replicates were used. The data were processed using EXCEL and plotted in SIGMAPLOT 11.0.

Example 5. NomadKin U2OS Stable Cell Line Development

Example 5: Results and Materials and Methods

Generation of Recombinant Stable Cell Line

The plasmid encoding the green $_{Kin}$Nomad biosensor was transfected into U2OS cells using LIPOFECTAMINELTX (Thermo Fisher Scientific, Waltham, MA). Resistant clones were obtained by limit dilution, and positively transfected cells were selected using 500 µg/ml GENETICIN (Sigma-Aldrich, St. Louis, MO). These cells constitutively expressed green $_{Kin}$Nomad biosensor.

Fluorescent images were acquired in the BD PATHWAY 855 High-Content automated image platform with a ×20 dry objective.

Example 6. Anti-TAC Immunofluorescence Assay of $Ca^{2+}$-Arrestin Multiplex "NTSR1 $_{Arres-Ca2+}$Nomad Biosensor Example 6. Results An anti-TAC immunofluorescence assay was performed to trace the localization of $_{Arrestin}$Nomad biosensor. The membrane localization of the biosensor observed in the control (upper panels) is difuminated in the activated cells (lower panels) with the agonist. The biosensor is relocalized from the plasma membrane to cytosolic vesicles.

Example 6. Materials and Methods

Cells were seeded at 12,000 cells/plate in 96-well black, clear-bottom imaging plates (BD Biosciences). "NTSR1 $_{Arrestin}$Nomad" cell line was treated with 1 µM of NTS (Sigma-Aldrich) in OPTI-MEM media (Gibco) for 24 hours at 37° C., 5% CO2, 95% relative humidity.

After overnight incubation, cell media was removed and it was performed a 15 minutes incubation with FBS (Sigma-Aldrich) at 4° C. Followed by a 90 minutes incubation at 4° C. with FITC anti-human CD25 antibody (Biolegend) at 1:20 concentration. Cells were then washed twice with PBS (Sigma-Aldrich). Fluorescent images were acquired in the BD PATHWAY 855 High-Content automated image platform (Franklin Lakes, NJ) with a ×20 dry objective. The excitation and emission filters used were the following: for FITC, 488/10 and 540/20; and for FP650, 548/20 and 570LP.

The invention claimed is:

1. A fluorescent fusion polypeptide capable of changing its localization and fluorescence intensity within a cell from the cell cytoplasmic membrane to the retention vesicles, upon an increase in translocation of beta-arrestin from the cell cytoplasm to the cell cytoplasmic membrane, comprising a membrane localization peptide consisting of the extracellular domain of interleukin-2 receptor of SEQ ID NO: 3; a peptide capable of binding G-protein or tyrosine receptors following phosphorylation of these receptors by GRKs or RTKs consisting of the phosphorylated receptor binding peptide from b-arrestin of SEQ ID NO: 2; a vesicularization peptide consisting of the Clathrin and beta-adaptin peptide from arrestin; and a fluorescent peptide wherein:

a. the membrane localization peptide is located at the N-terminus of the fluorescent fusion polypeptide and is physically bound, through a linker, to the fluorescent peptide, which in turn is physically bound, through a linker, to the peptide capable of binding G-protein or tyrosine receptors following phosphorylation of these receptors by GRKs or RTKs; and b. the peptide capable of binding G-protein or tyrosine receptors following phosphorylation of these receptors by GRKs or RTKs is physically bound, through a linker, to the vesicularization peptide, which in turn is located at the C-terminus of the fluorescent fusion polypeptide;

and wherein the term "membrane localization peptide" means a peptide whose natural intracellular localization is in the plasma membrane.

2. The fluorescent fusion polypeptide of claim 1, wherein the vesicularization peptide consisting of the Clathrin and beta-adaptin peptide from arrestin consists of SEQ ID NO: 4.

3. The fluorescent fusion polypeptide of claim 1, wherein:
c. the membrane localization peptide is the extracellular domain of interleukin-2 receptor of SEQ ID NO: 3; and
d. the vesicularization peptide consisting of the Clathrin and beta-adaptin peptide from arrestin consists of SEQ ID NO: 4.

4. The fluorescent fusion polypeptide of claim 1, wherein the fluorescent peptide is selected from the group consisting of GFP, YFP, turboGFP, turboRFP, turboRFP602 and turboRFP650.

5. A nucleic acid molecule comprising a polynucleotide sequence coding for a polypeptide as defined in claim 1.

6. A cell comprising the fluorescent polypeptide as defined in claim 1.

7. The cell of claim 6, wherein said cell is cell line U2OS (Human bone osteosarcoma cell line).

8. A method for detecting or recruiting beta arrestin, or both, comprising contacting the fluorescent polypeptide of claim 1 with a cell and monitoring the distribution of the polypeptide within cellular cytoplasm of the cell.

* * * * *